United States Patent
Nagamine et al.

(10) Patent No.: US 7,090,872 B2
(45) Date of Patent: Aug. 15, 2006

(54) ANTIOXIDANT, SKIN PREPARATION FOR EXTERNAL USE, COSMETIC AND FOOD

(75) Inventors: Kenichi Nagamine, Tokyo (JP); Miki Hayashi, Tokyo (JP); Kaori Yamasaki, Nagasaki (JP)

(73) Assignee: Nichirei Biosciences Inc., Tokyo (JP)

( * ) Notice: Subject to any disclaimer, the term of this patent is extended or adjusted under 35 U.S.C. 154(b) by 0 days.

(21) Appl. No.: 10/535,382

(22) PCT Filed: Nov. 21, 2003

(86) PCT No.: PCT/JP03/14885

§ 371 (c)(1),
(2), (4) Date: Jul. 22, 2005

(87) PCT Pub. No.: WO2004/048498

PCT Pub. Date: Jun. 10, 2004

(65) Prior Publication Data

US 2006/0051439 A1     Mar. 9, 2006

(30) Foreign Application Priority Data

Nov. 25, 2002   (JP) .............................. 2002-341191

(51) Int. Cl.
*A01N 65/00*  (2006.01)
*A01N 61/00*  (2006.01)
*A61K 36/00*  (2006.01)
*A61K 9/00*   (2006.01)
*A61K 6/00*   (2006.01)
*A61K 31/00*  (2006.01)
*C11B 5/00*   (2006.01)

(52) U.S. Cl. ...................... 424/725; 424/400; 424/401; 514/1; 426/541

(58) Field of Classification Search ................ 424/725, 424/400, 401; 426/541; 514/1
See application file for complete search history.

(56) References Cited

FOREIGN PATENT DOCUMENTS

| | | |
|---|---|---|
| JP | 02-200610 | 8/1990 |
| JP | 07-061915 | 3/1995 |
| JP | 2000-212026 | 8/2000 |
| JP | 2000-212027 A1 | 8/2000 |
| JP | 2000-212032 A1 | 8/2000 |
| JP | 2001-226218 | 8/2001 |

*Primary Examiner*—Michele Flood
*Assistant Examiner*—Amy L. Clark
(74) *Attorney, Agent, or Firm*—Darby & Darby (57) ABSTRACT

The invention relates to antioxidants that make effective use of acerola seeds, which have conventionally been discarded, that have high safety and excellent antioxidative effect in skin preparations for external use, cosmetics, and food, and that contain acerola seed extract as an active component. The invention also relates to skin preparations for external use, cosmetics, and food containing the antioxidant.

5 Claims, 5 Drawing Sheets

Fig. 1

Fraction 1 2 3 4 5 6 7 8 9 10 11 12 13 14 15 16 17 18 19 20

ANTIOXIDANT, SKIN PREPARATION FOR EXTERNAL USE, COSMETIC AND FOOD

FIELD OF ART

The present invention relates to antioxidants containing acerola seed extract as an active component, and to skin preparations for external use, cosmetics, and food prepared using the same.

BACKGROUND ART

Articles such as food, cosmetics, and medicines, that contain oils and fats, suffer from oxidation or peroxidation of the oil and fat components caused by atmospheric oxygen, which is the most serious problem in storage, preservation, and processing of such articles. Unsaturated fatty acids contained in oils and fats, such as linoleic and linolenic acids, are known to be particularly prone to peroxidation by oxygen to generate lipid peroxides, free radicals, or even carcinogenic substances. Oxidation and peroxidation cause not only coloration, discoloration, denaturalizaton, abnormal odor, or decrease in effective nutritional value of the articles, but also generation of toxic substances, which results in deterioration of product quality.

In order to inhibit such oxidation and peroxidation of unsaturated fatty acids, and to prevent deterioration of product quality, various antioxidants have conventionally been used. Antioxidants act on peroxide radicals, which are generated in oxidation, to terminate chain oxidation, or alternatively act on free radicals to terminate oxidative reaction. Commonly used antioxidants are synthetic antioxidants, such as butylhydroxyanisol (BHA) and butylhydroxytoluene (BHT). Recently, however, safety of synthetic antioxidants has come to be questioned as their use expands, and consumers are presenting growing rejections, which results in decrease in their amount of use. Further, synthetic antioxidants are oil soluble, and thus are hard to use in aqueous solutions.

On the other hand, as natural antioxidants of high safety, natural vitamin E ($\alpha$-tocopherol), vitamin C, and the like are known. However, these natural antioxidants are extremely fat- or water-soluble, so that their applications are limited. The natural antioxidants also have disadvantages in that their activity cannot be maintained stably for a prolonged period of time.

There is thus a strong demand for natural antioxidants having strong antioxidative activity, high water-solubility, and long-term stability in antioxidative activity.

Collagen and hyaluronic acid are known to have effects on moisture retaining property, softness, and elasticity of skin. Collagen constitutes 90% of dermis of skin and is distributed all over the dermis to give appropriate elasticity and strength to the skin. Hyaluronic acid is widely distributed over living organisms such as skin, synovial fluid, corpus vitreum, ligament, and the like, and contributes in skin to cell adhesion, cell protection, formation of skin tissues, retainment of tissue moisture, and maintenance of softness. Collagen and hyaluronic acid are known to be decomposed in vivo with enzymes called collagenase and hyaluronidase, respectively. It is said that, when these enzymes decompose collagen and hyaluronic acid to decrease their amounts, skin loses moisture and tension, and develops wrinkles and sagging, which are typical symptoms of skin ageing.

In expectation of anti-ageing and anti-wrinkle effects on skin, it is proposed to add substances that inhibit activities of these enzymes, to skin preparations for external use and various cosmetics, and various collagenase inhibitors and hyaluronidase inhibitors have been developed to date.

Recently, acerola fruit has come to be known as a vitamin C-rich plant, and has now been used in beverages and health foods around the world. The vitamin C-rich acerola fruit has also been in use in cosmetics for the expected antioxidative effect of vitamin C in the fruit extract (JP-2814094-B (JP-2-200610-A), JP-2000-212026-A, JP-2000-212027-A, and JP-2000-212032-A).

However, only the pulp of acerola fruit, which has a high vitamin C content, is used in cosmetics and food, and the seeds hardly find effective use and are mostly discarded. A cosmetic composition is recently proposed containing a steam distillate of plant seeds containing acerola seeds for improving skin feel (JP-2001-226218-A). Further effective use of acerola seeds is desired.

Incidentally, the constituting elements, effects, and the like of acerola seeds are hardly known yet.

SUMMARY OF THE INVENTION

It is therefore an object of the present invention to provide an antioxidant that makes effective use of acerola seeds, which have conventionally been discarded mostly, and that has high safety and excellent antioxidative effect in cosmetics, food, and the like.

It is another object of the present invention to provide a skin preparation for external use and cosmetics that are expected to have stable antioxidative effect, collagenase inhibitory effect, and hyaluronidase inhibitory effect, excellently safe, and expected to have anti-ageing and anti-wrinkle effects on skin.

It is still another object of the present invention to provide food that is expected to have stable antioxidative effect and is excellently safe.

In order to achieve the above objects, the present inventors have first made intensive studies for usefulness of acerola seeds, which have been discarded after the fruit is squeezed for juice. Through the studies, the inventors have found out that extract of acerola seeds has strong antioxidative capability, collagenase inhibitory effect, and hyaluronidase inhibitory effect, to thereby complete the present invention.

According to the present invention, there is provided an antioxidant, a collagenase inhibitor, or a hyaluronidase inhibitor, comprising acerola seed extract as an active component.

According to the present invention, there is also provided a skin preparation for external use or a cosmetic comprising the above antioxidant, or a skin preparation for external use or a cosmetic comprising at least one of the above antioxidant, collagenase inhibitor, and hyaluronidase inhibitor.

According to the present invention, there is further provided food comprising the above antioxidant.

PREFERRED EMBODIMENTS OF THE INVENTION

The present invention will now be explained in detail.

The antioxidant according to the present invention contains acerola seed extract as an active component. This extract is also useful as an active component of a collagenase inhibitor and a hyaluronidase inhibitor.

Acerola seeds are seeds of acerola (*Malpighia emarginata* DC) originated in the Caribbean West Indies in the Atlantic Ocean.

The pulp of acerola is known to be rich in vitamin C, and is used for food, cosmetics, and the like. However, the seeds of acerola have hardly found an effective use.

The acerola seed extract is not particularly limited as long as it is extracted, for example, with an extractant, and the method and conditions for extraction are not particularly limited as long as the resulting extract has an antioxidative capability, such as a linoleic acid autooxidation inhibitory effect and a DPPH radical scavenging activity. The place of production and breed of the acerola seeds are not at all limited, and those produced in, for example, Okinawa or Brazil may be used.

As used herein, acerola seed extract is a generic term for extracts prepared by crushing and processing raw, dried, or frozen acerola seeds, and extracting with water and/or an organic solvent; concentrates of such extracts; fraction-purified products of such extracts or concentrates obtained by fraction purification such as liquid-liquid extraction or column chromatography; and evaporation products thereof, in either a liquid, paste, or solid form.

The organic solvent used for preparing the extract may either be hydrophilic or hydrophobic. The hydrophilic organic solvent may be a conventional organic solvent, for example, alcohols, such as methyl alcohol, ethyl alcohol, glycerin, propylene glycol, and 1,3-butylene glycol, acetone, tetrahydrofuran, acetonitrile, 1,4-dioxane, pyridine, dimethylsulfoxide, N, N-dimethylformamide, or acetic acid. The hydrophobic organic solvent may be a conventional organic solvent, such as hexane, cyclohexane, carbon tetrachloride, chloroform, dichloromethane, 1,2-dichloroethane, diethyl ether, ethyl acetate, benzene, or toluene. One or a combination of two or more of these organic solvents may be used. Among these, water and/or a hydrophilic organic solvent, specifically, methanol, ethanol, 1,3-butylene glycol, water, or mixtures or combinations of these are particularly preferred.

The conditions for extraction are not particularly limited. For example, the temperature may be 5 to 95° C., preferably 10 to 90° C., more preferably 15 to 85° C., and even the room temperature will give good extraction. The extraction efficiency tends to be higher at higher temperatures. The extraction time may be a few hours to a few days, and the amount of solvent used for extraction is usually 1 to 20 times, preferably 2 to 10 times the amount of the raw material by weight.

The extraction operation is not particularly limited, and may be performed according to a common procedure. For improving the extraction efficiency, the extraction may be performed under shaking, or in an extraction device equipped with a stirrer or the like. For example, acerola seeds and an extractant may be stirred and shaken together, with or without preliminary soaking of the seeds in the extractant, and the resulting process liquid may be subjected to filtration, centrifugation, or decantation to separate the liquid into the extract liquid and the extract residue. The extract residue may further be subjected to a similar extraction process. The obtained extract liquid may be used as it is, or may further be concentrated and/or fractionated and purified, as desired.

The concentration process is not particularly limited, and may be performed by, for example, solvent removal, recovery of soluble components by making use of their solubility in water and/or an organic solvent, recovery of insoluble components, liquid-liquid separation with a water-hydrophobic organic solvent, recrystallization, reprecipitation, recovery of precipitate formed by cooling, or a combination of two or more of these.

The fractionation and purification process is not particularly limited, and may be performed by, for example, normal and/or reverse phase chromatography.

The acerola seed extract preferably contains quercitrin for use as an active component of the present antioxidant, and may contain quercitrin for use as an active component of the present collagenase inhibitor and hyaluronidase inhibitor.

In the antioxidant, as well as the collagenase inhibitor or hyaluronidase inhibitor of the present invention, the content of the acerola seed extract as an active component may suitably be selected depending on the form of use.

The skin preparation for external use and the cosmetics according to the present invention contain the present antioxidant. Further, skin preparations for external use or cosmetics containing at least one of the above antioxidant, collagenase inhibitor, and hyaluronidase inhibitor, may also be provided according to the invention.

The type of the cosmetics is not particularly limited, and may be, for example, skin care cosmetics such as skin lotion, emulsion, cream, face pack, and cleansing agents; make-up cosmetics such as lipsticks and foundation; or hair cosmetics. The cosmetics may be in any form without limitation. The skin preparation for external use may be, for example, ointment or various dermatological agents.

In the present skin preparation for external use and the cosmetics, the content of the present antioxidant, collagenase inhibitor, or hyaluronidase inhibitor may suitably be selected depending on their kind, the kind and amount of other components to be mixed, and the form of the agent. Usually, the content is 0.001 to 20 wt %, preferably 0.01 to 10 wt % of the total amount of the skin preparation for external use or the cosmetics, in terms of dried acerola seed extract.

The skin preparation for external use or the cosmetics according to the present invention may optionally contain various other components usually used as raw materials for skin preparations for external use or cosmetics, as long as the desired effect of the present invention is not impaired. Examples of such other components may include water, oil solutions, surfactants, lubricants, alcohols, water-soluble polymeric agents, gelatinizers, moisture retainers, buffers, preservatives, antiinflammatory agents, thickeners, flavoring agents, vitamins, and antioxidants other than those of the present invention. One or a combination of two or more of these may suitably be selected for use.

The food of the present invention may be of any type as long as the present antioxidant is contained, for example, candies, beverages, jam, or chewing gum. The food may be in any form without limitation.

In the food of the present invention, the content of the present antioxidant may suitably be selected depending on the kind of the food, the kind and amount of other components contained in the food, and the form of the food. Usually, the content is 0.001 to 20 wt %, preferably 0.01 to 10 wt % of the total amount of the food, in terms of dried acerola seed extract.

The food according to the present invention may optionally contain various other components usually used as raw materials for food, as long as the desired effect of the present invention is not impaired. Examples of such other components may include water, alcohols, sweeteners, acidulants, colorants, preservatives, flavoring agents, and excipients. One or more of these may suitably be selected for use.

The antioxidant, and also the hyaluronidase inhibitor and the collagenase inhibitor according to the present invention contain acerola seed extract as an active component, and have excellent safety and strong antioxidative effect, hyaluronidase inhibitory effect, or collagenase inhibitory effect. The skin preparations for external use, cosmetics, and food according to the present invention contain the present antioxidant, hyaluronidase inhibitor, or collagenase inhibitor, so that anti-ageing effect, anti-wrinkle effect, and quality improvement and preventive effects against oxidation of food caused by active oxygen, may be given. Further, effective use of acerola seeds, which have been an industrial waste, may be made.

EXAMPLES

The present invention will now be explained in more detail with reference to Examples, which are illustrative only and do not intend to limit the present invention.

Example 1

Acerola seeds were washed, dried, and crushed. 6140 g of the crushed product was mixed with sevenfold weight of methanol, and stirred at room temperature overnight. The entire mass was centrifuged and filtered. The filtrate was concentrated and evaporated to dry, to obtain 225.89 g of extract (A).

Extract (A) thus obtained was mixed with 2000 ml of water and further with 1200 ml of hexane and shaken. The separated aqueous layer was recovered, mixed with hexane, and shaken in the same way as above. This operation was repeated twice. The aqueous layer separated from the hexane layer was mixed with 1200 ml of ethyl acetate and shaken, which operation was repeated ten times. The separated ethyl acetate layers were collected, concentrated, and evaporated to dry, to thereby obtain 11.48 g of concentrate (A). Subsequently, the concentrate (A) was fractionated by silica gel chromatography on a column of silica gel (Wakosil C-300, manufactured by WAKO PURE CHEMICAL INDUSTRIES, LTD.), and the fractions were eluted in sequence with chloroform, chloroform:methanol (97:3, 9:1, 8:2, 6:4, 4:6, 2:8), and methanol. The chloroform eluate was divided into fifteen fractions (Fractions 1 to 15), and the subsequent chloroform:methanol eluate was taken as Fractions 16 (97:3), 17 (9:1), 18 (8:2), 19 (6:4), and 20 (4:6).

The antioxidative activity of each fraction was determined by evaluation using thin layer chromatography (TLC). Specifically, a sample of each fraction was applied to a silica gel thin layer plate, and developed with a developing solvent. Here, plates with a fluorescence indicator (K5F Silica Gel 150 Å, manufactured by WHATMAN PLC) were used. After the development, the dried plate was irradiated with UV to detect the spots on the sample having UV absorption. Then the plate was sprayed with a $6\times10^{-4}$ M methanol solution of a stable radical, diphenyl-p-picrylhydradil (DPPH). The violet color of the DPPH solution is lost when the radicals are scavanged. Thus the plate is observed decolorized on the spots of substances having radical scavenging activity due to the scavenging of the DPPH radical.

Figure 1:
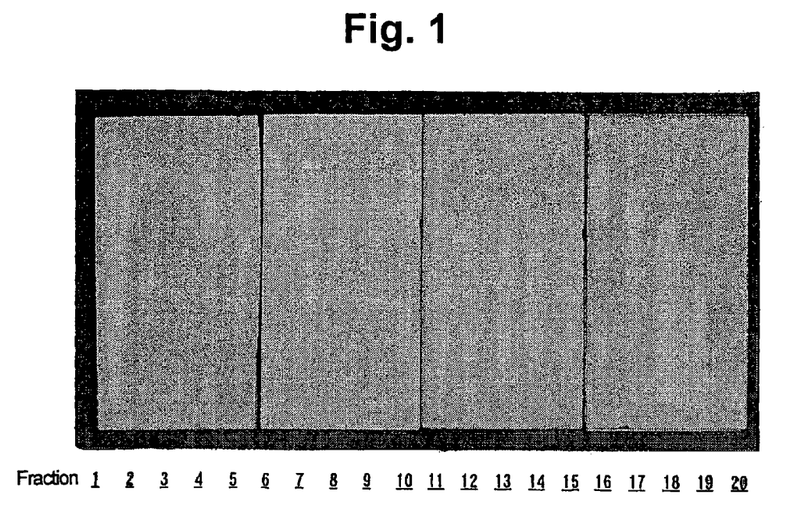
FIG. 1 is a photocopy of a thin layer chromatogram showing the antioxidative activity of each fraction from column chromatography of acerola seed extract prepared in Example 1.

Fractions 1 to 20 were applied to silica gel plates, the plates were developed to their tips with a chloroform:methanol (9:1) solvent, and the DPPH solution was sprayed over the plates. The results are shown in FIG. 1. From this figure, it is understood that the acerola seed extract contains a number of substances having antioxidative activity.

Then Fraction 19 was further purified by reverse phase high performance liquid chromatography (HPLC). Specifically, the sample was first subjected to crude purification under the following elution conditions, and then to purification under the following conditions. The conditions for the HPLC are shown below.

Column: Hydrosphere C-18 [20×250 mm] (YMC), Flow Rate: 5 ml/min., Temperature: 35° C., Detection: UV at 254 nm, Eluent: 30% methanol (0–2 min), 30–100% methanol (2–32 min, linear), 100% methanol (32–40 min), and 30% methanol (40–50 min). After the crude purification under the above conditions, the crude product was finally purified with acetonitrile/water (30/70) to give 72 mg of a fraction purified product.

Various spectral measurements were performed on the obtained fraction purified product. The obtained data are shown below:

Mass Spectrum: [M−H]−447

Ultraviolet Absorption Spectrum: (EtOH) 256.5 nm, 352.00 nm, H-NMR Chemical shift: 500 MHz, solvent $CD_3OD$, 0.94 ppm (d:J=6.1 Hz), 6.91 ppm (d:J=8.2 Hz), 7.31 ppm (d, d:J=8.2, 2.1 Hz), 7.34 ppm (d:J=2.1 Hz), 6.20 ppm (d:J=2.1 Hz), 6.37 ppm (d:J=2.1 Hz), 3.33 ppm (m:J=9.5, 9.3 Hz), 3.41 ppm (m:J=9.5 Hz), 3.74 ppm (d, d:J=9.3, 3.3 Hz), 4.21 ppm (d, d:J=3.3 Hz), 5.35 ppm (d:J=1.7 Hz), C-NMR chemical shift: 125.8 MHz, solvent $CD_3OD$, 17.7 ppm, 72.0 ppm, 72.1 ppm, 72.2 ppm, 73.3 ppm, 94.8 ppm, 99.9 ppm, 103.6 ppm, 106.0 ppm, 116.4 ppm, 117.0 ppm, 122.9 ppm, 123.1 ppm, 136.3 ppm, 146.5 ppm, 149.9 ppm, 158.6 ppm, 159.4 ppm, 163.3 ppm, 166.0 ppm, 179.7 ppm.

In the mass spectrum, ions which appear to be deprotonated molecules were observed at m/z447, and thus the molecular weight of the sample was believed to be 448. In H-NMR, the peak at 0.94 ppm was attributed to $^1H$ of $CH_3$, the peaks at 6.91 ppm, 7.31 ppm, and 7.34 ppm to $^1H$ of 1,2,4-substituted benzene, and the peaks at 6.20 ppm and 6.37 ppm to $^1H$ of 1,2,3,5-substituted benzene. Five peaks were observed in 3.33–5.35 ppm. Further, in $^{13}C$-NMR spectrum, 21 peaks were observed. Among them, four peaks in 70–74 ppm appeared to be >CH—O—, and at 179.7 ppm a peak attributed to conjugated carbonyl was observed. These data suggested that the sample could possibly be a quercetin glycoside. Thus the high-resolution mass spectrum of the sample was further measured, and the NMR spectrum of the sample was compared with that of a quercitrin sample, which is known to be a quercetin glycoside having a molecular weight of 448. As a result of the measurement of high-resolution mass spectrum, a precise weight of 447.0917 was obtained, and the composition was calculated with C, H, and O being the elemental species. The calculation gave a composition $C_{21}H_{19}O_{11}$, which satisfied the carbon number 21 observed in the $^{13}C$-NMR spectrum. Thus the molecular formula was determined to be $C_{21}H_{19}O_{11}$. Further, the NMR spectrum of the sample was compared with that of a quercitrin (quercetin-3-rhamnoside) sample, and found to match. Thus the substance isolated and purified from the acerola seed extract was identified as quercitrin.

Quercitrin is a flavonoid commonly found in nature, and known to be contained in *Houttuynia cordata* at a particularly high content. From the results above, it was determined that quercitrin is contained in acerola seeds, and is one of the substances that contribute to the antioxidative activity of the extract.

Example 2

100 g of washed acerola seeds were crushed, mixed with threefold volume of water, and shaken at room temperature overnight. The entire mass was filtered through a glass filter, a 0.65 μm filter, and a 0.22 μm filter, and the filtrate was concentrated and evaporated to dry, to thereby obtain 1 g of an extract.

Next, the antioxidative activity of the obtained extract was measured by antioxidative activity measurement using linoleic acid (ferric thiocyanate method).

Specifically, a mixture of 0.4 mg of the acerola seed extract, 2 ml of 99.5% ethanol, and 2 ml of distilled water was mixed with a reaction liquid composed of 2 ml of 2.5% (w/v) linoleic acid (99.5% ethanol solution) and 4 ml of a 0.05 M phosphate buffer (pH 7.0), and placed in a brown threaded bottle, to thereby prepare 10 ml of a test liquid. On the other hand, test liquids as positive controls were prepared in the same way using α-tocopherol or BHA in place of the acerola seed extract at the same content in the reaction liquid. A test liquid as a control was prepared by mixing with the reaction liquid only 2 ml of 99.5% ethanol and 2 ml of distilled water without the acerola seed extract. The test liquids thus prepared were stored in darkness at 40° C. as main samples, and at 4° C. as blanks. Samples were taken out at intervals, and measured by the following methods. The test lasted for 14 days.

First, to a mixture of 0.1 ml of the sample, 9.7 ml of 75% ethanol, and 0.1 ml of a 30% aqueous solution of ammonium rhodanide, 0.1 ml of $2\times10^{-2}$ M ferrous chloride (3.5% hydrochloric acid solution) was added, and exactly 3 minutes later, the absorbance at 500 nm was measured. The same measurement was made with the blanks, and Δabsorbance was taken according to the following formula:

Δ absorbance=(absorbance of main sample)−(absorbance of blank).

The absorbance increases with oxidation of the sample, and after reaching the maximum, decreases with consumption of the sample to be oxidized. Thus earlier occurrence of the peak absorbance represents weaker antioxidative activity.

Further, the antioxidative activities of the test liquids were compared using the degree of oxidation. The degree of oxidation was calculated according to the following formula, with the oxidation of the control (Δ absorbance) being as 100%. Higher degree of oxidation represents lower antioxidative activity.

Degree of Oxidation (%)=([Δ absorbance of sample]/[Δ absorbance of control])×100

Figure 2:
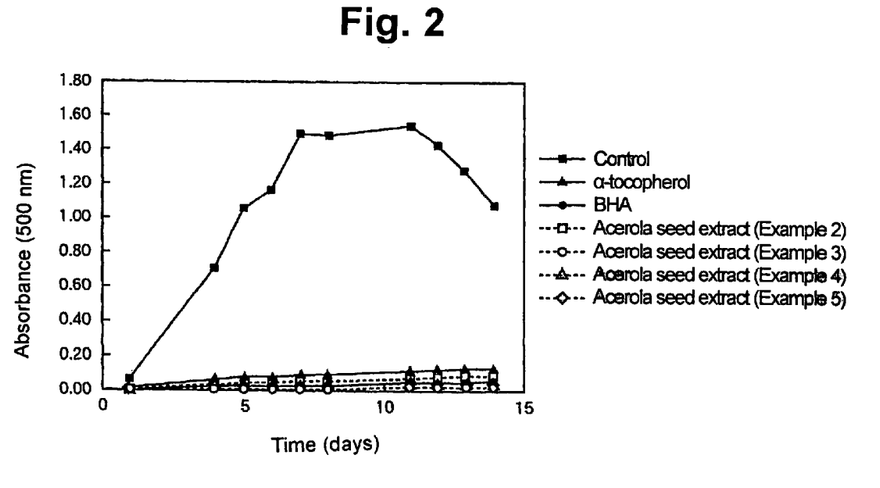
FIG. 2 is a graph showing the change in absorbance against time for determining the degree of oxidation of the acerola seed extracts prepared in Examples 2 to 5.
Figure 3:
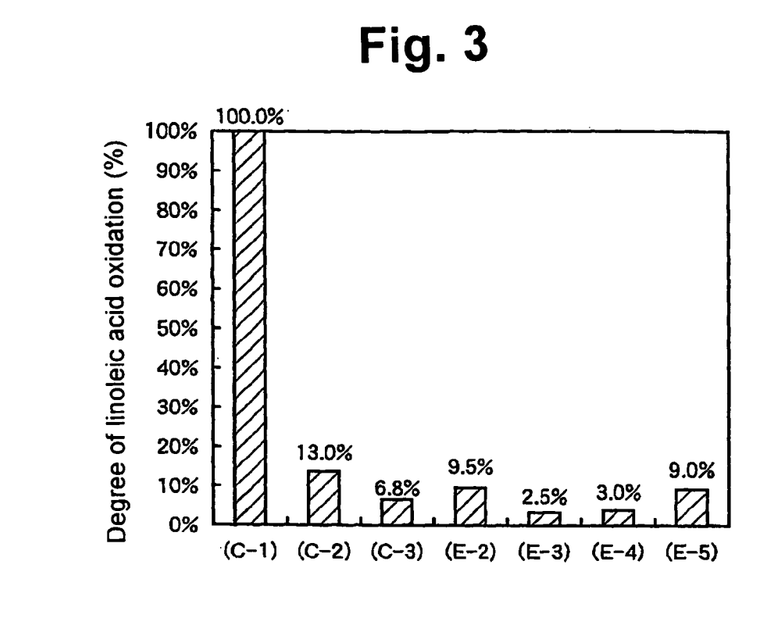
FIG. 3 is a graph showing the degree of oxidation on day 14 of the acerola seed extracts prepared in Examples 2 to 5.

The change in absorbance against time is shown in FIG. 2, and the degree of oxidation of each sample on day 14 of the test is shown in FIG. 3. In FIG. 3, (C-1) refers to the control, (C-2) to the sample with α-tocopherol, (C-3) to the sample with BHA, (E-2) to the sample with the acerola seed extract prepared in Example 2, (E-3) to the sample with the acerola seed extract prepared in Example 3, (E-4) to the sample with the acerola seed extract prepared in Example 4, and (E-5) to the sample with the acerola seed extract prepared in Example 5.

Example 3

100 g of washed acerola seeds were crushed, mixed with threefold volume of a 25 vol % aqueous solution of ethanol, and shaken at room temperature overnight. The entire mass was filtered through the same filters as in Example 2, and the filtrate was concentrated and evaporated to dry, to thereby obtain 1.69 g of an extract.

The antioxidative activity of the obtained extract was measured in the same way as in Example 2. The change in absorbance against time is shown in FIG. 2, and the degree of oxidation of the sample on day 14 of the test is shown in FIG. 3.

Example 4

100 g of washed acerola seeds were crushed, mixed with threefold volume of a 50 vol % aqueous solution of ethanol, and shaken at room temperature overnight. The entire mass was filtered through the same filters as in Example 2, and the filtrate was concentrated and evaporated to dry, to thereby obtain 2.27 g of an extract.

The antioxidative activity of the obtained extract was measured in the same way as in Example 2. The change in absorbance against time is shown in FIG. 2, and the degree of oxidation of the sample on day 14 of the test is shown in FIG. 3.

Example 5

100 g of washed acerola seeds were crushed, mixed with threefold volume of a 75 vol % aqueous solution of ethanol, and shaken at room temperature overnight. The entire mass was filtered through the same filters as in Example 2, and the filtrate was concentrated and evaporated to dry, to thereby obtain 2.50 g of an extract.

The antioxidative activity of the obtained extract was measured in the same way as in Example 2. The change in absorbance against time is shown in FIG. 2, and the degree of oxidation of the sample on day 14 of the test is shown in FIG. 3.

From FIGS. 2 and 3, it is understood that the acerola seed extracts evidently have an inhibitory effect on linoleic acid oxidation, and that the magnitude of the inhibitory effect is the same as or even larger than that of a typical antioxidant, α-tocopherol and BHA. Further, from the results in Examples 2 to 5, it is understood that the magnitude of antioxidative activity may be controlled by changing the ethanol content of the aqueous ethanol solution used as the extractant.

Example 6

760 g of washed acerola seeds were crushed, mixed with fivefold weight of methanol, and stirred at room temperature overnight. The entire mass was centrifuged and filtered, and the filtrate was concentrated and evaporated to dry, to thereby obtain 12.36 g of an extract. To the extract, 300 ml of water and then 100 ml of hexane were added and shaken. The separated aqueous layer was recovered, mixed with hexane, and shaken in the same way as above. This operation was repeated three times. The aqueous layer separated from the hexane layer was mixed with 100 ml of ethyl acetate and shaken, which operation was repeated six times. The separated ethyl acetate layers were collected, concentrated, and evaporated to dry, to thereby obtain 0.41 g of solid.

Figure 4:
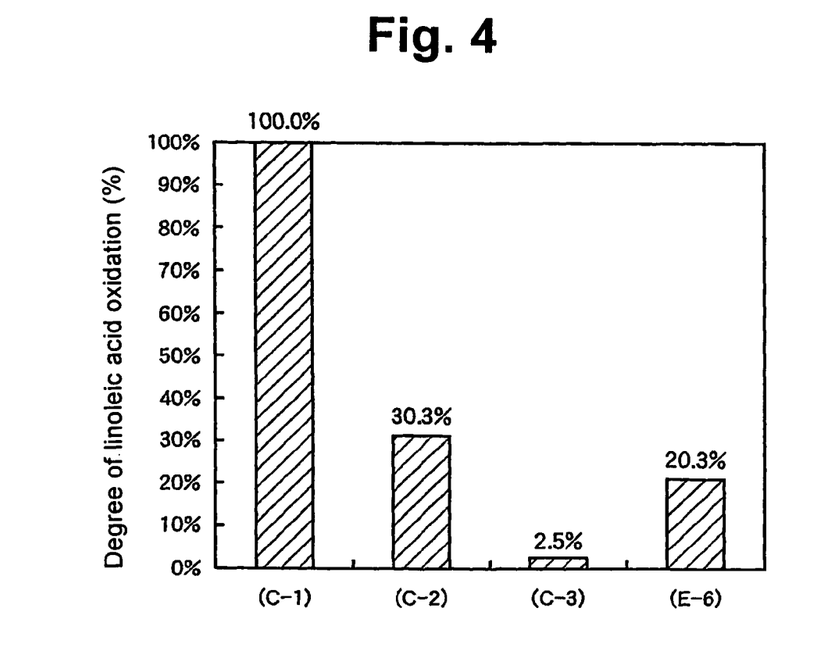
FIG. 4 is a graph showing the degree of oxidation on day 20 of the acerola seed extract prepared in Example 6.

The antioxidative activity of the acerola seed extract thus obtained was measured by the ferric thiocyanate method in the same way as in Example 2. Here, the test lasted for 20 days. The degree of oxidation of each sample on day 20 of the test is shown in FIG. 4. In FIG. 4, (C-1) refers to the control, (C-2) to the sample with α-tocopherol, (C-3) to the sample with BHA, and (E-6) to the sample with the acerola seed extract prepared in Example 6.

From FIG. 4, it is understood that the ethyl acetate fraction of the acerola seed extract evidently has an inhibitory effect on linoleic acid oxidation as with the extract per se, and that the magnitude of the inhibitory effect is larger than that of α-tocopherol.

Example 7

70 g of washed acerola seeds were crushed, mixed with fourfold weight of a 30 wt % aqueous solution of 1,3-butylene glycol, and stirred at room temperature overnight. The entire mass was centrifuged, and the supernatant was filtered through a 0.22 μm filter, to thereby obtain 124.12 g of acerola seed extract in a solution form.

The antioxidative activity of the acerola seed extract thus obtained was measured by the DPPH radical scavenging method discussed below. The results are shown in Table 1.

1600 μl of a 250 mM acetate buffer (pH 5.5) was mixed with 1200 μl of ethanol and 400 μl of a sample (prepared at an arbitrary concentration), and pre-incubated at 30° C. for 5 minutes. 800 μl of a 500 μM DPPH/ethanol solution was added, left to stand at 30° C. for 30 minutes, and measured for the absorbance at 517 nm. The same procedure was performed with α-tocopherol, and the resulting product was used as a positive control. The same procedure was also performed with the sample solution being replaced with its extractant, and the resulting product was used as a control. The radical scavenging ratio was calculated from the measured absorbances in accordance with the following formula:

Scanvenging ratio (%)=(1−[absorbance of sample]/[absorbance of control])×100

The scavenging ratios were measured with the sample concentration in the sample solution being changed stepwise, to determine the concentration of the sample solution at which the DPPH radical scavenging ratio was 50%. This concentration was taken as the 50% DPPH radical scavenged concentration. A lower value of this concentration means higher radical scavenging activity.

TABLE 1

| Sample Measured | 50% DPPH radical scavenged concentration (μg/ml) |
|---|---|
| Extract of Example 7 | 115.24 |
| α-tocopherol | 110.13 |

From Table 1, it is understood that the extract of Example 7 has radical scavenging activity equivalent to that of α-tocopherol.

Example 8

1500 g of washed acerola seeds were crushed, mixed with twofold weight of a 30 wt % aqueous solution of 1,3-butylene glycol, and stirred at room temperature overnight. The entire mass was centrifuged, and the supernatant was filtered through a 0.22 μm filter, to thereby obtain 2327 g of acerola seed extract in a solution form.

The antioxidative activity of the obtained acerola seed extract was measured by the ferric thiocyanate method in the same way as in Example 2. Here, the acerola seed extract, which was in a solution form, was diluted with water and ethanol to the required concentration before being added. As a control against the acerola seed extract solution, a solution having the same solvent composition as that of the acerola seed extract solution but without the acerola seed extract, was used. The test lasted for 7 days.

Figure 5:
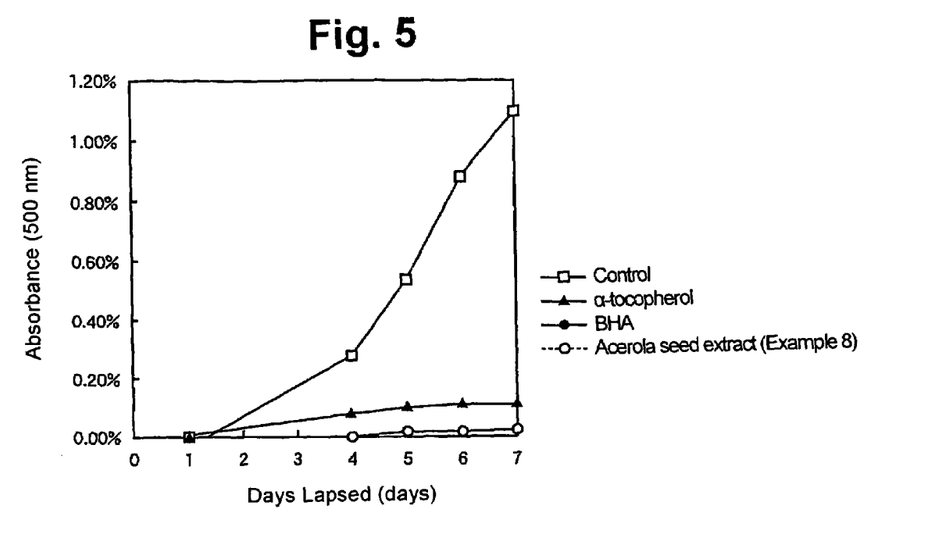
FIG. 5 is a graph showing the change in absorbance against time for determining the degree of oxidation of the acerola seed extract prepared in Example 8.
Figure 6:
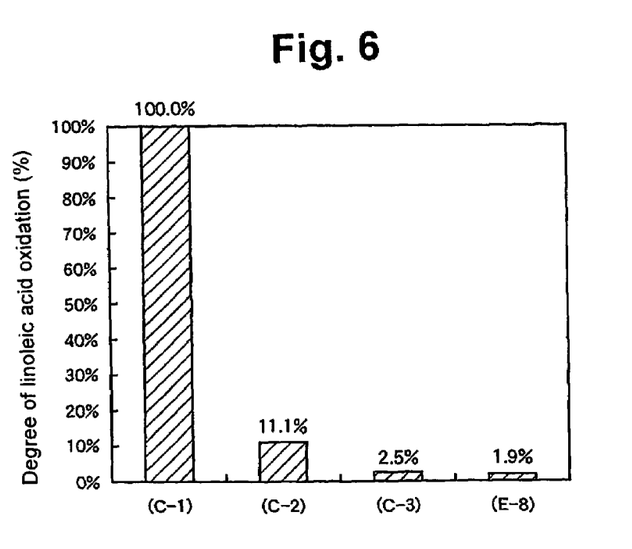
FIG. 6 is a graph showing the degree of oxidation on day 7 of the acerola seed extract prepared in Example 8.

The change in absorbance against time is shown in FIG. 5, and the degree of oxidation of each sample solution on day 7 of the test is shown in FIG. 6. In FIG. 6, (C-1) refers to the control, (C-2) to the sample with a-tocopherol, (C-3) to the sample with BHA, and (E-8) to the sample with the acerola seed extract prepared in Example 8.

From FIGS. 5 and 6, it is understood that the acerola seed extract evidently has an inhibitory effect on linoleic acid oxidation, and that the magnitude of the inhibitory effect is the same or even larger than that of a-tocopherol or BHA.

Incidentally, since vitamin C is conventionally known to have an antioxidative effect, the vitamin C content of the acerola seed extract solution prepared above was measured for investigation as to whether the antioxidative effect of the above acerola seed extract solution was ascribable solely to vitamin C.

First, the vitamin C content of 100 g of the acerola seed extract solution prepared above was measured, and found to be 57 mg/100 g (56 mg/100 g of dehydroascrobic acid+1 mg/100 g of ascorbic acid). Then, 100 g of the acerola seed extract solution was evaporated to dry to obtain 975 mg of solid. The antioxidative activity was measured by the ferric thiocyanate method in the same way as in Example 2. Here, the acerola seed extract, which was in a solution form in this Example, was diluted in the same way as above before being added, so that 0.4 mg of the solid is contained in the reaction liquid. As a control, a solution having the same solvent composition as that of the acerola seed extract solution but without the acerola seed extract, was used. The test lasted for 7 days. As a comparison, the antioxidative activity of the vitamin C contained in 0.4 mg of the above solid, i.e. 0.023 mg (0.4 mg×(57 mg/975 mg)) of vitamin C, was also measured.

The degree of oxidation on day 7 of the test was 1.9% for the acerola seed extract, and 115.8% for vitamin C alone.

From these results, it was demonstrated that the vitamin C contained in the acerola seed extract hardly contributed to the antioxidative effect of the extract.

Further, the acerola seed extract prepared above was measured in the same way as in Example 1 for quercitrin, which is one of the substances having an antioxidative effect as confirmed in Example 1. As a result, the acerola seed extract prepared above was also found to contain quercitrin.

It is reported, for example in JP-7-300581-A, that quercitrin has an antioxidative activity. In view of this fact, it was investigated whether the antioxidative effect of the above acerola seed extract solution was ascribable solely to quercitrin.

Since quercitrin is a polyphenol, the polyphenol content of the acerola seed extract solution prepared above was measured by the Folin-Denis method. It was found that the polyphenol content in 975 mg of the solid per 100 g of the extract solution was 25%. Thus the quercitrin content in the solid in the acerola seed extract solution prepared above is at most 25%. Based on this result, the antioxidative activity was measured by the ferric thiocyanate method in the same way as in Example 2, in a manner similar to the above comparative experiment with vitamin C. Here, the test lasted for 7 days. As a comparison, the antioxidative activity of 0.128 mg of quercitrin was measured in the same way, which amount was based on the assumption that 0.4 mg of the solid contained 32% of quercitrin (more than the maximum of 25%).

The result was that the degree of oxidation on day 7 of the test was 1.9% for the acerola seed extract, and 6.9% for quercitrin alone.

From these results, it was demonstrated that the quercitrin contained in the acerola seed extract was one of the active components for the antioxidative activity of the extract, but not the sole contributor. What is more, it was demonstrated that the antioxidative activity of the acerola seed extract was superior to that of quercitrin alone.

Referential Example 1

The collagenase inhibitory effect of each of the acerola seed extracts prepared in Examples 2 to 5 was measured in the following process.

Process of Measurement

Preparation of Reagent

Substrate solution: 0.39 mg of Pz-peptide (manufactured by BACHEM AG) was dissolved in 1 ml of a 0.1 M Tris-HCl buffer (pH 7.1, containing 20 mM calcium chloride) for use (equivalent to 0.5 mM).

Enzyme solution: 5 mg of collagenase (TYPE IV, manufactured by SIGMA) was dissolved in 1 ml of distilled water, divided into aliquots of 100 μm each, and stored at −20° C. Each aliquot was diluted 50 times with distilled water upon use for reaction.

Method for Measuring Collagenase Inhibitory Effect

Sample solutions were prepared by dissolving the extract prepared in Example 2 in its extractant at a concentration of 15 mg/ml, and the extract prepared in each of Example 3, 4, and 5 with its extractant at a concentration of 0.5 mg/ml. 50 μl of each sample solution, 50 μl of the collagenase solution, and 400 μl of the substrate solution were mixed, and incubated at 37° C. for 30 minutes. Then the reaction was terminated with 1 ml of a 25 mM citric acid solution, and the resulting solution was extracted with 5 ml of ethyl acetate. After centrifuging (3000 rpm, 10 minutes), the absorbance of the ethyl acetate layer at 320 nm was measured, using ethyl acetate as a standard. As a control against each sample solution, its extractant was used. A blank for each solution was prepared by the same operation, with the enzyme solution being replaced with distilled water.

From the obtained values, the degree of inhibition of collagenase activity was calculated in accordance with the following formula:

Degree of inhibition (%)=$[1-(A-B)/(C-D)] \times 100$ wherein A stands for the absorbance of the sample solution at 320 nm, B of the blank for the sample solution at 320 nm, C of the control solution at 320 nm, and D of the blank for the control solution at 320 nm.

According to the above method, the degree of inhibition of collagenase activity by the extracts prepared in Examples 2 to 5 was obtained. The results are shown in Table 2.

TABLE 2

| Sample | Concentration (mg/ml) | Degree of inhibition of collagenase activity (%) |
| --- | --- | --- |
| Example 2 | 15 | 35.9 |
| Example 3 | 0.5 | 78.0 |
| Example 4 | 0.5 | 76.6 |
| Example 5 | 0.5 | 78.9 |

Referential Example 2

The collagenase inhibitory activity of the acerola seed extract prepared in Example 8 was measured in the same way as in Referential Example 1. Here, the extract of Example 8, which was in a solution form, was diluted with its extractant, i.e., a 30 wt % aqueous solution of 1,3-butylene glycol, so that the content of the acerola seed extract as solid was 0.5 mg/ml, to prepare a sample solution. In this way, the degree of inhibition of collagenase activity by the extract prepared in Example 8 was determined to be 71.5%.

Referential Example 3

The hyaluronidase inhibitory effect of the extract prepared in Example 8 was measured by the method of Yumie Maeda et al. (Shokueishi, Vol. 31, p233–237, 1990), which is based on the Morgan-Elson method.

Process of Measurement

[Preparation of Reagents]

Enzyme solution: Bovine testis hyaluronidase (manufactured by WAKO PURE CHEMICAL INDUSTRIES, LTD.) was dissolved in a 0.1 M acetate buffer (pH 4.0) to have a final enzymatic activity of 400 Units/ml.

Enzyme activator solution: Compound 48/80 (manufactured by SIGMA) was dissolved in a 0.1 M acetate buffer (pH 4.0) to have a final concentration of 0.1 mg/ml.

Substrate solution: Potassium hyaluronate (manufactured by WAKO PURE CHEMICAL INDUSTRIES LTD.) was dissolved in a 0.1 M acetate buffer (pH 4.0) to have a final concentration of 0.4 mg/ml.

Boric acid solution: 50 ml of water was added to 4.95 g of boric acid, the pH was adjusted to 9.1 with a 1N sodium hydroxide solution, and the volume was adjusted to 100 ml with water.

p-Dimethyl-aminobenzaldehyde (p-DAB) reagent: 10 g of p-DAB (manufactured by WAKO PURE CHEMICAL INDUSTRIES LTD.) was dissolved in a mixture of 12.5 ml of 10 N hydrochloric acid and 87.5 ml of acetic acid, and refrigerated. The solution was diluted ten times with acetic acid immediately before use.

[Measurement of Hyaluronidase Inhibitory Effect]

The extract prepared in Example 8, which was in a solution form, was diluted with its extractant, i.e., a 30 wt % aqueous solution of 1,3-butylene glycol, so that the content of the acerola seed extract as solid was 1 mg/ml, to prepare a sample solution. 0.1 ml of the enzyme solution was added to 0.2 ml of this sample solution, and left to stand at 37° C. for 20 minutes. Then 0.2 ml of the enzyme activator solution was added, and warmed at 37° C. for 20 minutes. 0.5 ml of the substrate solution was added, and reacted at 37° C. for 40 minutes. Then the reaction was stopped by adding 0.2 ml of a 0.4 N aqueous solution of sodium hydroxide and ice-cooling. 0.2 ml of a boric acid solution was added, and heated in a hot block bath (TOYO SEISAKUSHO, Model TPB-32) at 100 to 120° C. for 5 minutes, and then ice-cooled. 6 ml of p-DAB reagent was added, and heated at 37° C. for 20 minutes to develop coloration. The absorbance at 585 nm was measured, using distilled water as a standard. In a control, the sample solution was replaced with its extractant, and in corresponding blanks for the sample and the control, the enzyme solution was replaced with a 0.1 M acetate buffer (pH=4.0), and treated in the same way.

From the obtained values, the degree of inhibition of hyaluronidase activity was calculated in accordance with the following formula:

Degree of Inhibition (%)=[1−(A−B)/(C−D)]×100 wherein A stands for the absorbance of the sample solution at 585 nm, B of the blank for the sample solution at 585 nm, C of the control solution at 585 nm, and D of the blank for the sample solution at 585 nm.

According to the above method, the degree of inhibition of hyaluronidase activity of the extract prepared in Example 8 was found to be 94.5%.

Referential Example 4

A safety test was conducted on acerola seed extract in accordance with The Ordinance No. 21 regarding Good Laboratory Practice dated Mar. 26, 1997, by Ministry of Health and Welfare, Japan. The acerola seed extract used here was the one prepared in Example 8. The results are shown in Table 3.

Single Oral Dose Toxicity Study in Rats

Two groups (control and administered groups) of rats each consisting of five males and five females were used. The administered group was given 2 g/kg body weight of the extract.

Skin Primary Irritation Test in Guinea Pigs

Three guinea pigs were exposed to the extract by occlusive patch on healthy skin for 24 hours. At 24, 48, and 72 hours after the administration, the skin conditions were observed and evaluated.

14-Day Skin Accumulative Irritation Test in Guinea Pigs

Three guinea pigs were exposed to the extract by application on healthy skin once a day in an open system for 14 consecutive days. During the test period, the skin conditions were observed and evaluated every day at 24 hours before and after the application.

Skin Sensitization Study in Guinea Pigs

Three groups of guinea pigs (control, applied, and DNCB groups) consisting of 5 animals each were tested in accordance with the Adjuvant and Patch Test method, and the skin conditions were observed and evaluated at 24 and 48 hours after the application.

Skin Phototoxicity Study in Guinea Pigs

Ten guinea pigs were tested on the back skin in accordance with the method of Fujiou Morikawa, et al., and the skin conditions were observed and evaluated at 24, 48, and 72 hours after the UV irradiation.

Skin Photosensitization Study in Guinea Pigs

Three groups of guinea pigs (control, administered, and TCSA groups) consisting of 5 animals each, were tested in accordance with the Adjuvant and Strip method, and the skin conditions were observed and evaluated at 24 and 48 hours after the UV irradiation.

Eye Mucosal Irritation Test in Rabbits

Two groups of rabbits (non-eyewashed and eyewashed groups) consisting three animals each were used. After administration of the eye drops, the non-eyewashed group was not treated, while the eyewashed group was subjected to eye flush with tipid saline for about 1 minutes. At 1, 24, 48, and 72 hours after that, the conditions of the cornea, iris, and conjunctiva were observed, and evaluated in accordance with the AFNOR standard.

Reverse Mutation Test in Bacteria

Measurements were made in accordance with the preincubation assay with or without S9mix added.

Bacterial strains used: *Salmonella typhimurium* TA100, TA98, TA1535, TA 1537

Bacterial strains used: *Escherichia coli* WP2uvrA

Chromosomal Aberration Assay in Cultured Mammalian Cells

Three groups (negative control, tested substance, and positive control groups) of cultured mammalian cells (CHL/IU cells) were used, and evaluated by the short-term treatment method (6 hours of treatment, with or without S9mix added) and the continuous treatment method (24 and 48 hours of treatment).

TABLE 3

| List of Safety Tests | Results |
| --- | --- |
| 1) Single oral dose toxicity study in rats | not toxic |
| 2) Skin primary irritation test in guinea pigs | not irritative |
| 3) 14-Day skin accumulative irritation test in guinea pigs | not irritative |
| 4) Skin sensitization study in guinea pigs | not sensitizable |
| 5) Skin phototoxicity study in guinea pigs | not phototoxic |
| 6) Skin photosensitization study in guinea pigs | not photosensitizable |
| 7) Eye mucosal irritation test in rabbits | not eye irritative |
| 8) Reverse mutation test in Bacteria | not mutagenic |
| 9) Chromosomal aberration assay in cultured mammalian cells | no aberration |

Prescription Example 1

0.20 parts by weight of dipotassium glycyrrhizinate, 0.10 parts by weight of citric acid, 0.30 parts by weight of sodium citrate, 5.00 parts by weight of the acerola seed extract prepared in Example 7, and 5.00 parts by weight of 1,3-butylene glycol were mixed, and purified water was added to increase the total amount to 80.0 parts by weight. The mixture was dissolved under stirring at 50° C. to prepare an extract-containing aqueous solution.

0.90 parts by weight of tetraoleic acid-POE (60) sorbitol, 0.10 parts by weight of sorbitan monooleate, a suitable amount of preservative, and 10.00 parts by weight of ethanol were mixed, and dissolved under stirring at 50° C. Then the obtained solution was added in small portions to the previously-prepared extract-containing aqueous solution, and mixed under stirring at 50° C. until the mixture became homogeneous. The temperature of the solution was lowered under stirring from 50° C. to 30° C., where the stirring was stopped. Suitable amounts of flavoring agents and purified water were added to increase the total amount to 100.00 parts by weight. Then the mixture was stirred again into a homogeneous mixture to prepare a skin lotion.

Prescription Example 2

10.00 parts by weight of squalene and a suitable amount of preservative were mixed, purified water was added to increase the total amount to 70.00 parts by weight, and the resulting mixture was heated to 80° C. to prepare solution (1). On the other hand, 0.10 parts by weight of carboxyvinyl polymer and 0.20 parts by weight of xanthan gum were dissolved in a suitable amount of purified water under stirring at room temperature to prepare solution (2). 0.10 parts by weight of triethanol amine and 5.00 parts by weight of 1,3-butylene glycol were dissolved in a suitable amount of purified water under stirring at room temperature to prepare solution (3). 2.00 parts by weight of sodium hyaluronate and 5.00 parts by weight of the acerola seed extract prepared in Example 8 were dissolved in a suitable amount of purified water under stirring at room temperature to prepare solution (4).

Next, solution (1) was added in small portions into a suitable amount of purified water, and mixed under stirring at 80° C. Solution (2), and then solution (3) were successively added under stirring. When mixed homogenously, the mixture was cooled to 50° C. under stirring, where solution (4) was added, and purified water was added to increase the total amount to 100 parts. The resulting solution was stirred again until the temperature is lowered to 30° C., where the stirring was stopped, to obtain a homogenous emulsion.

Prescription Example 3

2.00 parts by weight of POE(20) sorbitan monostearate, 0.50 parts by weight of POE sorbitan tetraoleate, 0.50 parts by weight of glyceryl monostearate, 7.00 parts by weight of stearic acid, 3.00 parts by weight of cetyl alcohol, 3.00 parts by weight of cetyl palmitate, 7.00 parts by weight of jojoba oil, 3.00 parts by weight of paraffin, and a suitable amount of preservative were mixed, and dissolved under stirring at 80° C. to prepare solution (1). On the other hand, 5.00 parts by weight of the acerola seed extract prepared in Example 8, 7.00 parts by weight of 1,3-butylene glycol, and 62 parts by weight of purified water were mixed, and dissolved under stirring at 80° C. to prepare solution (2).

Then, solution (1) was added in small portions into solution (2), emulsified, cooled under stirring to 40° C., where the stirring was stopped, to prepare a homogenous cream.

Prescription Example 4

100 g of concentrated grapefruit juice, 150 g of sugars, 15 g of honey, 1.5 g of acerola seed extract (A) prepared under the same conditions as in Example 2, and a suitable amount of flavoring agents were mixed with purified water so that the total amount was 1000 g. Then the mixture was sterilized at 95° C. for 20 minutes, and packed aseptically in bottles by 100 ml, to thereby give a grapefruit juice.

Prescription Example 5

0.6 parts by weight of POE(30) POP(6) decyltetradecyl ether, 10.0 parts by weight of ethanol, and 0.1 parts by weight of methylparaben were mixed under stirring at 50° C. On the other hand, 0.1 parts by weight of sodium citrate, 1.0 parts by weight of sodium pyrrolidone carboxylate, 4.4 parts by weight of 1,3-butyleneglycol, and a suitable amount of purified water were mixed under stirring at 50° C. The latter solution was added to the former solution, and cooled to 30° C. under stirring. Further, 2.0 parts by weight of the acerola seed extract prepared in Example 8 was added and mixed under stirring, and a suitable amount of purified water was added to increase the total amount to 100 parts by weight. The solution was stirred into a homogeneous mixture, to prepare a skin lotion.

Prescription Example 6

A skin lotion was prepared in the same way as in Prescription Example 5, except that the contents of 1,3-butylene glycol and the acerola seed extract prepared in Example 8 were changed to 3.5 parts by weight and 5.0 parts by weight, respectively.

Comparative Prescription Example 1

A skin lotion was prepared in the same way as in Prescription Example 5, except that the content of 1,3-butylene glycol was changed to 5.0 parts by weight, and the acerola seed extract prepared in Example 8 was not added.

Example 9

The skin lotion prepared in Prescription Example 5 was subjected to measurement of inhibitory effect on linoleic acid oxidation by the ferric thiocyanate method as in Example 2. By way of comparison, the skin lotion without acerola seed extract prepared in Comparative Prescription Example 1 was also subjected to the same measurement of inhibitory effect on oxidation.

In this Example, 0.4 mg of the acerola seed extract, 2 ml of 99.5% ethanol, and 2 ml of distilled water mixed with the reaction liquid in Example 2 were replaced with 2 ml of the skin lotion prepared in Prescription Example 5 or Comparative Prescription Example 1, 1.8 ml of 99.5% ethanol, and 0.2 ml of distilled water in the test.

Figure 7:
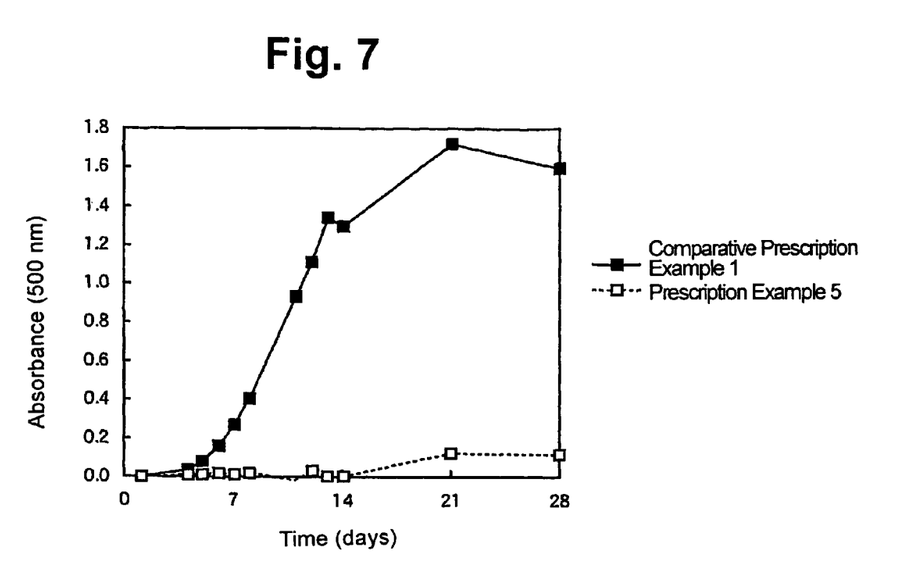
FIG. 7 is a graph showing the change in absorbance of the skin lotions prepared in Prescription Example 5 and Comparative Prescription Example 1 against time for determining the degree of oxidation thereof conducted in Example 9.

The change in absorbance against time is shown in FIG. 7. The degree of oxidation on day 28 of the test of the skin lotion sample prepared in Prescription Example 5 was calculated in the same way as in Example 2, with respect to the degree of oxidation on day 21 (Δ absorbance) of the skin lotion sample prepared in Comparative Prescription Example 1 being 100%. The degree of oxidation was found to be 7.2%.

FIG. 7 and the results of the test on the degree of oxidation clearly show that the skin lotion with the acerola seed extract prepared in Prescription Example 5 exhibited superior inhibitory effect on linoleic acid oxidation, compared to the skin lotion prepared in Comparative Prescription Example 1, and that the activity was maintained even after 28 days.

It was demonstrated that the skin lotion with acerola seed extract had excellently stable antioxidative activity.

Example 10

In order to confirm the durability and availability of the antioxidative activity of a skin lotion with acerola seed extract even after the lapse of more than one month from its preparation, the skin lotions prepared in Prescription Examples 5 and 6 and Comparative Prescription Example 1 were stored under the following conditions for 6 months. After the storage, the change in DPPH radical scavenging activity was evaluated by means of the antioxidative activity test as in Example 7.

Storage Conditions

The skin lotions prepared in Prescription Examples 5 and 6 were stored in darkness at 4° C., 25° C., and 40° C. for 6 months from the preparation. The samples were subjected to the DPPH radical scavenging test immediately after the preparation, two weeks after the preparation, and one, two, three, four, and six months after the preparation. By way of comparison, the skin lotion prepared in Comparative Prescription Example 1 was also stored and tested in the same way.

In this Example, 400 μl of the acerola seed extract mixed with the reaction liquid in Example 7 was replaced with 400 μl of the skin lotion prepared in Prescription Example 5 or 6 in the test. Incidentally, the DPPH radical scavenging ratio (%) was calculated in the same way as in Example 7 against the absorbance of a control sample, wherein the skin lotion prepared in Prescription Example 5 or 6 was replaced with the skin lotion prepared in Comparative Prescription Example 1 stored under the same conditions.

Figure 8:
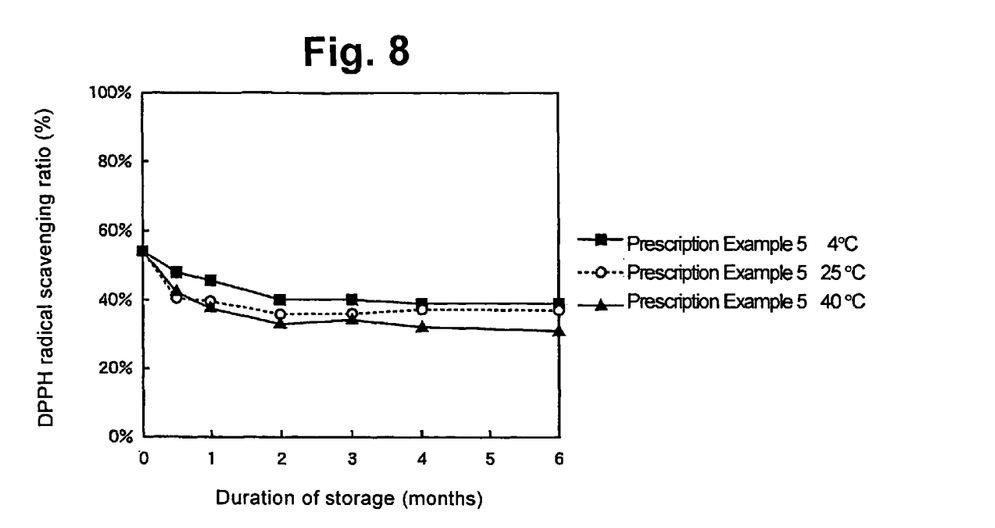
FIG. 8 is a graph showing the results of the DPPH radical scavenging test on the skin lotion of Prescription Example 5 conducted over six months in Example 10.
Figure 9:
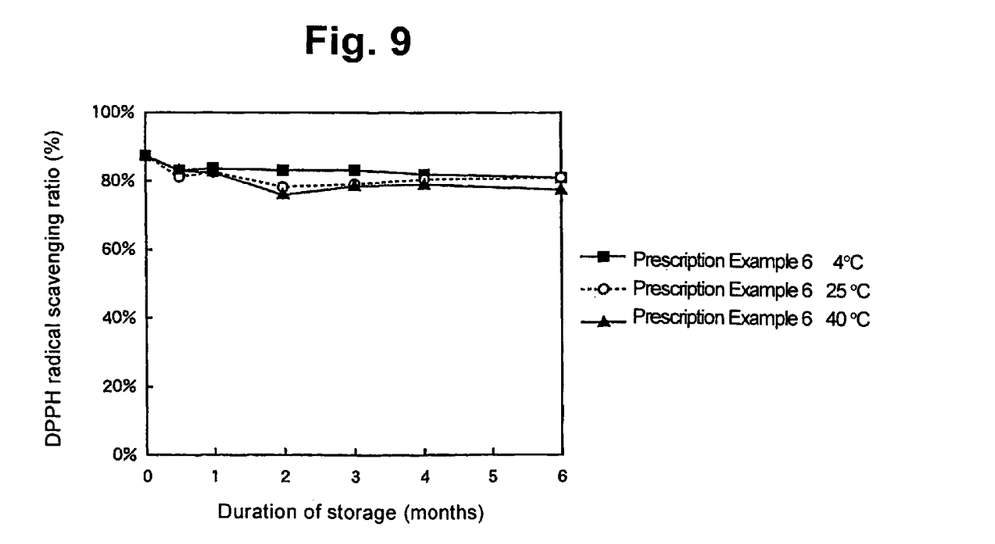
FIG. 9 is a graph showing the results of the DPPH radical scavenging test on the skin lotion of Prescription Example 6 conducted over six months in Example 10.

The results of the DPPH radical scavenging tests conducted over 6 months on the skin lotions prepared in Prescription Examples 5 and 6 are shown in FIGS. 8 and 9, respectively.

FIGS. 8 and 9 clearly show that the skin lotions with acerola seed extract prepared in Prescription Examples 5 and 6 had excellent DPPH radical scavenging activity, and that the activity was not lost even after the 6 months of storage under as severe conditions as at 40° C. Further, the skin lotion with a higher content of acerola seed extract prepared in Prescription Example 6 showed still higher antioxidative activity with superior durability.

From the above results, it was demonstrated that the skin lotions with acerola seed extract had excellent antioxidative activity that survives long-term storage, particularly at high temperatures, and that this activity is expected to be higher at a higher content of acerola seed extract.

What is claimed is:

1. An antioxidant comprising acerola seed extract as an active component.
2. The antioxidant of claim 1, wherein said acerola seed extract contains quercitrin.
3. A skin preparation for external use comprising the antioxidant of claim 1.
4. A cosmetic comprising the antioxidant of claim 1.
5. A food comprising the antioxidant of claim 1.

* * * * *